US010689480B2

(12) United States Patent
Hidaka

(10) Patent No.: US 10,689,480 B2
(45) Date of Patent: Jun. 23, 2020

(54) LIQUID-CRYSTAL COMPOUND, THERMALLY RESPONSIVE MATERIAL, AND PRODUCTION METHOD THEREFOR

(71) Applicant: TOYO TIRE & RUBBER CO., LTD., Itami-shi, Hyogo (JP)

(72) Inventor: Yuki Hidaka, Itami (JP)

(73) Assignee: TOYO TIRE CORPORATION, Itami-shi (JP)

( * ) Notice: Subject to any disclaimer, the term of this patent is extended or adjusted under 35 U.S.C. 154(b) by 0 days.

(21) Appl. No.: 16/073,107

(22) PCT Filed: Mar. 1, 2016

(86) PCT No.: PCT/JP2016/056196
§ 371 (c)(1),
(2) Date: Jul. 26, 2018

(87) PCT Pub. No.: WO2017/149640
PCT Pub. Date: Sep. 8, 2017

(65) Prior Publication Data
US 2019/0127509 A1    May 2, 2019

(51) Int. Cl.
| | |
|---|---|
| C08G 18/48 | (2006.01) |
| C07C 43/23 | (2006.01) |
| C07C 245/08 | (2006.01) |
| C09K 19/14 | (2006.01) |
| C09K 19/24 | (2006.01) |
| C09K 19/12 | (2006.01) |
| C09K 19/22 | (2006.01) |
| C07C 251/24 | (2006.01) |
| C07C 235/56 | (2006.01) |
| C08G 18/32 | (2006.01) |
| C08G 18/38 | (2006.01) |
| C08G 18/72 | (2006.01) |
| C08G 18/73 | (2006.01) |
| C08G 18/76 | (2006.01) |

(52) U.S. Cl.
CPC ......... *C08G 18/4879* (2013.01); *C07C 43/23* (2013.01); *C07C 235/56* (2013.01); *C07C 245/08* (2013.01); *C07C 251/24* (2013.01); *C08G 18/3215* (2013.01); *C08G 18/3819* (2013.01); *C08G 18/3836* (2013.01); *C08G 18/48* (2013.01); *C08G 18/722* (2013.01); *C08G 18/73* (2013.01); *C08G 18/7614* (2013.01); *C09K 19/12* (2013.01); *C09K 19/14* (2013.01); *C09K 19/22* (2013.01); *C09K 19/24* (2013.01); *C08G 2250/00* (2013.01)

(58) Field of Classification Search
CPC .. C09D 171/00; C09D 171/02; C09D 171/12; C09D 171/14; C09D 171/03; C09D 171/08; C08G 65/2663; C08G 65/1202; C08G 65/2603; C08G 65/2606; C08G 65/2618; C08G 65/2636; C08G 65/2639
See application file for complete search history.

(56) References Cited

U.S. PATENT DOCUMENTS

| | | | |
|---|---|---|---|
| 4,791,187 A | 12/1988 | Suling et al. | |
| 6,723,393 B1 | 4/2004 | Niyama et al. | |
| 2004/0019224 A1 | 1/2004 | Dershem et al. | |
| 2006/0119783 A1 | 6/2006 | Fukuoka et al. | |
| 2007/0286968 A1 | 12/2007 | Takeuchi et al. | |
| 2018/0171233 A1* | 6/2018 | Iseki | C09K 19/2007 |

FOREIGN PATENT DOCUMENTS

| | | | |
|---|---|---|---|
| JP | 63-051413 A | 3/1988 | |
| JP | 2-268129 A | 11/1990 | |
| JP | 5-170860 A | 7/1993 | |
| JP | 6-136088 A | 5/1994 | |
| JP | 6-507987 A | 9/1994 | |
| JP | 7-258369 A | 10/1995 | |
| JP | 2000-119656 A | 4/2000 | |
| JP | 2004-264322 A | 9/2004 | |
| JP | 2005-194427 A | 7/2005 | |
| JP | 2008-19240 A | 1/2008 | |
| JP | 2010-150440 A | 7/2010 | |
| JP | 2013-245321 A | 12/2013 | |

(Continued)

OTHER PUBLICATIONS

Onouchi et al., "Preparation and Physical Properties of Polyurethane Elastomers Containing Mesogenic Moieties", Preparation and Physical Properties of PU Elastomers Containing Mesogenlc Moiethes, Oct. 1995, pp. 30-36, Japanese Notification of Reasons for Refusal dated Feb. 22, 2018 (7 pages).

Mitsumata et al., "Synthesis and Properties of Thermotropic Liquid Crystalline Polyurethanes Containing Azobenzene Group as a Mesogenic Unit", Journal of Technological Researches edited by the College of Engineering, Kanta Gakuin University, 2003, vol. 47-1, pp. 33-37, Japanese Notification of Reasons for Refusal dated Feb. 22, 2018, w/English translation (15 pages).

(Continued)

*Primary Examiner* — Shane Fang
(74) *Attorney, Agent, or Firm* — Westerman, Hattori, Daniels & Adrian, LLP

(57) ABSTRACT

One purpose of the present invention is to provide a liquid-crystal compound which exhibits liquid crystallinity at low temperatures. Another purpose of the present invention is to provide a thermally responsive material which exhibits liquid crystallinity and rubber elasticity at low temperatures (around room temperature) ever, though a large amount of a liquid-crystal compound is contained therein, and a method for producing this thermally responsive material. A liquid-crystal compound according to the present invention is obtained by adding an alkylene oxide and/or styrene oxide to a mesogenic group-containing compound that has an active hydrogen group.

9 Claims, No Drawings

(56) References Cited

FOREIGN PATENT DOCUMENTS

| JP | 2014-172967 A | 9/2014 |
|---|---|---|
| JP | 2014-177621 A | 9/2014 |
| JP | 2016-56113 A | 4/2016 |
| WO | 93/22397 A1 | 11/1993 |
| WO | 2015/093099 A1 | 6/2015 |

OTHER PUBLICATIONS

Jia et al., "Synthesis and Properties of Main-Chain Liquid Crystalline Polyurethane Elastomers with Azoxybenzene", Journal of Applied Polymer Science, 1996, vol. 62, pp. 465-471, Japanese Notification of Reasons for Refusal dated Feb. 22, 2018 (7 pages).
Padmavathy et al., "Synthesis and Characterization of Thermotropic Liquid Crystalline Main-Chain Polyurethanes rom High-Aspect Ratio Mesogenic Diols", Macromolecular Chemistry and Physics, 2001, vol. 202, No. 12, pp. 2538-2546, Japanese Notification of Reasons for Refusal dated Feb. 22, 2018 (9 pages).
Sudhakar et al., "Novel Thermotropic Liquid Crystalline Polyurethanes From Mesogenic Diols: Synthesis and Characterization", Proceedings of the IUPAC International Symposium on Advances in Polymer Science and Technology, 1998, vol. 1, pp. 232-235, Japanese Notification of Reasons for Refusal dated Feb. 22, 2018 (5 pages).
Lee et al., "Self-Organization of Rod-Coil Molecules into a Bicontinuous Cubic Liquid Crystalline Phase", Molecular Crystals and Liquid Crystals, 1999, vol. 332, pp. 2593-2600, Japanese Notification of Reasons for Refusal dated Feb. 22, 2018 (8 pages).
Strehmel, "Model Reactions and Formation of Epoxy Networks with the Phenylbenzoate Mesogen", Journal of Jolymer Science, Part A: Polymer Chemistry, 1997, vol. 35, pp. 2653-2688, Japanese Notification of Reasons of Refusal dated Feb. 22, 2018 (36 pages).
Cendejas et al., "Novel initiators for the synthesis of propylene oxide oligomers by anionic ring opening Polymerization", Catalysis Today, 2008, vol. 130, pp. 486-491, Japanese Notification of Reasons for Refusal dated Feb. 22, 2018 (6 pages).
Koscielny et al, "Synthesis and characterization of glycidyl ethers modified by mesogenic units", Polymer Bulletin, 1994, vol. 32, 529-536, Japanese Notification of Reasons for Refusal dated Feb. 22, 2018 (8 pages).
Notification of Reasons for Refusal dated Feb. 22, 2018, issued in Japanese Patent Application No. 2014-181611, w/English translation (14 pages).
Notification of Reasons for Refusal dated May 22, 2018, issued in Japanese Patent Application No. 2014-181611, w/ English translation (5 pages).
International Search Report dated May 17, 2016, issued in counterpart International Application No. PCT/JP2016/056196 (3 pages).
Notification of Transmittal of Translation of the International Preliminary Report on Patentability (Form PCT/IB/338) issued in counterpart International Application No. PCT/JP2016/056196 dated Sep. 13, 2018 with Forms PCT/IB/373 and PCT/ISA/237. (13 pages).

* cited by examiner

LIQUID-CRYSTAL COMPOUND, THERMALLY RESPONSIVE MATERIAL, AND PRODUCTION METHOD THEREFOR

TECHNICAL FIELD

The present invention relates to a liquid-crystal compound, a themotropic thermally responsive material, and a production method therefor.

BACKGROUND ART

A liquid-crystal elastomer is a hybrid material of liquid-crystals and elastomers. The liquid-crystal elastomer shows a characteristic response behavior in such a manner that the liquid-crystal elastomer is extended in the orientation direction by applying an external stimulus such as heat, light, electric field, and magnetic field to increase the degree of liquid-crystal orientation, but the liquid-crystal elastomer is shrunk by removing such a stimulus to decrease the degree of liquid-crystal orientation. Thus, applications of such an elastomer to various fields such as actuators and the like have been attempted.

For example, Patent Document 1 discloses a high-molecular liquid-crystal polyurethane exhibiting liquid crystallinity, which is obtained by reacting a bis(ω-hydroxy-alkyleneoxy)biphenyl with 1,4-phenylene diisocyanate.

Further, Patent Document 2 discloses a polymer liquid-crystal polyurethane obtained by polymerizing a diol component having a mesogenic group with a trans-1,4-cyclohexane diisocyanate.

However, in the conventional liquid-crystal polyurethane, the temperature at which a liquid-crystal is developed is very high and it was difficult to develop liquid crystallinity at a low temperature (near room temperature). Further, the conventional liquid-crystal polyurethane did not exhibit rubbery elasticity due to increased fluidity when a liquid-crystal is developed therein. Further, the conventional mesogenic diol as a starting material has a high temperature at which liquid crystallinity is exhibited and was difficult to produce a liquid-crystal polyurethane without a solvent.

PRIOR ART DOCUMENTS

Patent Documents

Patent Document 1: JP-A-H5-170860

SUMMARY OF THE INVENTION

Problems to be Solved by the Invention

One purpose of the present invention is to provide a liquid-crystal compound which exhibits liquid crystallinity at low temperatures. Another purpose of the present invention is to provide a thermally responsive material which exhibits liquid crystallinity and rubber elasticity at low temperatures (around room temperature) even though a large amount of a liquid-crystal compound is contained therein, and a method for producing this thermally responsive material.

Means for Solving the Problems

The inventors of the present invention have made extensive and intensive studies to solve the above problems, and, as a result, have found that the purpose of the present invention can be achieved by the following liquid-crystal compound and thermally responsive material. The present invention has been completed based on these findings.

The present invention relates to a liquid-crystal compound obtained by adding an alkylene oxide and/or styrene oxide to a mesogenic group-containing compound that has an active hydrogen group.

The inventor of the present invention found that addition of an alkylene oxide and/or a styrene oxide to a mesogenic group-containing compound having an active hydrogen group reduces the thermal stability of the mesogenic group, so that the temperature range exhibiting the liquid crystallinity is lowered. By using the liquid-crystal compound, reaction curing can be carried out without a solvent and in a state where liquid crystallinity is exhibited. By the reaction curing in a state in which liquid crystallinity is exhibited, it is possible to inhibit the crystallinity of a mesogen and prevent the formation of a crystalline phase.

In the present invention, it is preferable that the mesogenic group-containing compound is a compound represented by a general formula (1) below:

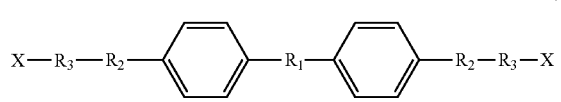

(1)

wherein X is an active hydrogen group; $R_1$ is a single bond, —N=N—, —CO—, —CO—O—, or —CH=N—; $R_2$ is a single bond or —O—; and $R_3$ is a single bond or an alkylene group having 1 to 20 carbon atoms, provided that the compound when $R_2$ is —O— and $R_3$ is a single bond is excluded.

In addition, it is preferable that the alkylene oxide is at least one kind selected from the group consisting of ethylene oxide, propylene oxide, and butylene oxide.

In addition, it is preferable that 2 to 10 moles of the alkylene oxide and/or styrene oxide are added to 1 mole of the compound represented by the general formula (1). When the number of moles added is less than 2 moles, it becomes difficult to sufficiently lower the temperature range in which the liquid crystallinity of the liquid-crystal compound is exhibited, and there is a tendency that it is difficult to react and cure in a state in which liquid crystallinity is exhibited without any solvent. On the other hand, when the number of moles added exceeds 10 moles, the liquid-crystal compound tends to fail to exhibit the liquid crystallinity.

The thermally responsive material of the present invention is obtained by reacting the liquid-crystal compound with a compound capable of reacting with an active hydrogen group of the liquid-crystal compound and exhibits liquid crystallinity and rubber elasticity at low temperatures (around room temperature).

The thermally responsive material preferably contains 50 to 90% by weight of the liquid-crystal compound as a raw material, more preferably 60 to 80% by weight. By increasing the blending amount of the liquid-crystal compound and increasing the content of the mesogenic group, a thermally responsive material which greatly deforms due to temperature change can be obtained. In the present invention, even when the content of the liquid-crystal compound is increased, the thermally responsive material obtained has a low elastic modulus because the liquid-crystal compound described above is used. When the content of the liquid-crystal compound is less than 50% by weight, the liquid crystallinity tends to be hardly exhibited. On the other hand, when the content of the liquid-crystal compound exceeds 90% by weight, it is difficult to introduce a crosslinking point into the molecule, so that curing is hard to proceed.

The transition temperature (Ti) from a liquid-crystal phase to an isotropic phase or from the isotropic phase to the liquid-crystal phase of the thermally responsive material is preferably from 0 to 100° C.

In addition, the present invention relates to a method for producing a thermally responsive material, the method comprising:

a step A of adding an alkylene oxide and/or styrene oxide to a mesogenic group-containing compound having an active hydrogen group to obtain a liquid-crystal compound;

a step B of mixing the liquid-crystal compound and a compound that reacts with the active hydrogen group of the liquid-crystal compound under no solvent condition to obtain a raw material composition for a thermally responsive material; and a step C of curing the raw material composition for a thermally responsive material at a temperature at which liquid crystallinity is exhibited.

In the method for producing a thermally responsive material of the present invention, it is preferable that the mesogenic group-containing compound is a compound represented by a general formula (1) below:

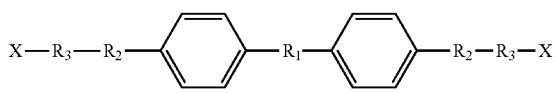

(1)

wherein X is an active hydrogen group; $R_1$ is a single bond, —N═N—, —CO—, —CO—O—, or —CH═N—; $R_2$ is a single bond or —O—; and $R_3$ is a single bond or an alkylene group having 1 to 20 carbon atoms, provided that the compound when $R_2$ is —O— and $R_3$ is a single bond is excluded.

In addition, it is preferable that the alkylene oxide is at least one kind selected from the group consisting of ethylene oxide, propylene oxide, and butylene oxide.

In addition, it is preferable that 2 to 10 moles of the alkylene oxide and/or styrene oxide are added to 1 mole of the compound represented by the general formula (1).

The content of the liquid-crystal compound in the raw material composition for a thermally responsive material is preferably from 50 to 90% by weight, more preferably from 60 to 80% by weight. By increasing the blending amount of the liquid-crystal compound to increase the content of the mesogenic group, it is possible to obtain a thermally responsive material which greatly deforms due to temperature change. In the present invention, even when the content of the liquid-crystal compound is increased, the thermally responsive material obtained has a low elastic modulus because the liquid-crystal compound mentioned above is used. When the content of the liquid-crystal compound is less than 50% by weight, the liquid crystallinity tends to be hardly exhibited. On the other hand, when the content of the liquid-crystal compound exceeds 90% by weight, it is difficult to introduce a crosslinking point into the molecule, so that curing is hard to proceed.

In addition, it is preferable that the raw material composition for a thermaLly responsive material is cured at a temperature at which liquid crystallinity is exhibited so that the mesogenic group of the liquid-crystal compound is oriented in step C.

Effect of the Invention

The liquid-crystal compound of the present invention has a low temperature range in which liquid crystallinity is exhibited. By using the liquid-crystal compound, it is possible to react and cure in a state in which liquid crystallinity is exhibited without any solvent. The thermally responsive material of the present invention has a low temperature range in which the liquid crystallinity of the liquid-crystal compound as a starting material is exhibited and has a network structure by crosslinking, so that said material has liquid crystallinity and rubber elasticity at low temperatures (in the vicinity of room temperature). Since the mesogenic group of the thermally responsive material is oriented in a uniaxial direction, said material shows a characteristic response behavior such that it shrinks by a decrease in the degree of the mesogenic group orientation due to heat applied thereto and extends in the orientation direction by an increase in the degree of the mesogenic group orientation due to removal of the heat applied.

MODE FOR CARRYING OUT THE INVENTION

The liquid-crystal compound of the present invention is a compound obtained by adding an alkylene oxide and/or styrene oxide to a mesogenic group-containing compound having an active hydrogen group.

The mesogenic group-containing compound having an active hydrogen group is not particularly limited as long as it is a compound having an active hydrogen group and a mesogenic group, but said mesogenic group-containing compound is preferably a compound represented by the following general formula (1):

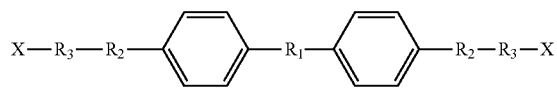

(1)

wherein X is an active hydrogen group; $R_1$ is a single bond, —N═N—, —CO—, —CO—O—, or —CH═N—; $R_2$ is a signle bond or —O—; and $R_3$ is a single bond or an alkylene group having 1 to 20 carbon atoms, provided that the compound when $R_2$ is —O— and $R_3$ is a single bond is excluded.

Examples of X include OH, SH, $NH_2$, COOH, secondary amines, and the like.

In order to obtain a thermally responsive material having a transition temperature (Ti) of 0 to 100° C. from a liquid-crystal phase to an isotropic phase or from the isotropic phase to the liquid-crystal phase, it is preferable to use a compound having a biphenyl skeleton ($R_1$ is a single bond). When $R_3$ is an alkylene group, the number of carbon atoms is preferably 2 to 10.

The alkylene oxide to be added is not particularly limited, and examples thereof include ethylene oxide, propylene oxide, 1,2-butylene oxide, 2,3-butylene oxide, cyclohexene oxide, epichlorohydrin, epibromohydrin, methyl glycidyl ether, allyl glycidyl ether, and the like. The styrene oxide to be added may have a substituent such as an alkyl group, an alkoxyl group, or a halogen on the benzene ring.

In order to obtain a thermally responsive material having a transition temperature (Ti) of 0 to 100° C. at which phase transition from a liquid-crystal phase to an isotropic phase or from the isotropic phase to the liquid-crystal phase occurs, it is preferable to use at least one oxide selected from the group consisting of ethylene oxide, propylene oxide, 1,2-butylene oxide, 2,3-butylene oxide, and styrene oxide.

The alkylene oxide and/or the styrene oxide is preferably added in an amount of 2 to 10 moles, more preferably 2 to 8 moles, with respect to 1 mole of the compound represented by the general formula (1).

The transition temperature (Ti) from a liquid-crystal phase to an isotropic phase or from the isotropic phase to the liquid-crystal phase of the liquid-crystal compound is preferably from 15 to 150° C., more preferably from 25 to 125° C.

The liquid-crystal compound may be used singly or in combination of two or more thereof.

The thermally responsive material of the present invention is a material obtained by reacting the liquid-crystal compound with a compound that reacts with an active hydrogen group of the liquid-crystal compound. Examples of the compound that reacts with the active hydrogen group of the liquid-crystal compound include an isocyanate compound, an epoxy compound, a silanol group-containing compound, a halide, a carboxylic acid, an alcohol, and the like. In particular, it is preferable to use an isocyanate compound. Hereinafter, the thermally responsive material will be described by exemplifying a liquid-crystal polyurethane elastomer.

The known compounds in the field of polyurethanes can be used as the isocyanate compound which is a raw material of a liquid-crystal polyurethane elastomer without any particular limitation. The isocyanate compounds include, for example, aromatic diisocyanates such as 2,4-toluene diisocyanate, 2,6-toluene diisocyanate, 2,2'-diphenyl methane diisocyanate, 2,4'-diphenyl methane diisocyanate, 4,4'-diphenyl methane diisocyanate, 1,5-naphthalene diisocyanate, p-phenylene diisocyanate, m-phenylene diisocyanate, p-xylylene diisocyanate and m-xylylene diisocyanate, aliphatic diisocyanates such as ethylene diisocyanate, 2,2,4-trimethyl hexamethylene di isocyanate and 1,6-hexamethylene diisocyanate, and cycloaliphatic diisocyanates such as 1,4-cyclohexane diisocyanate, 4,4'-dicyclohexyl methane diisocyanate, isophorone diisocyanate and norbornane diisocyanate. These may be used alone or as a mixture of two or more thereof.

In order to introduce a crosslinking point into the liquid-crystal polyurethane elastomer to form a network, it is preferable to use a tri- or more functional isocyanate compound in combination, and it is particularly preferable to use a trifunctional isocyanate compound in combination. The isocyanate compounds having a functionality of 3 or more include, for example, triisocyanates (e.g., triphenylmethane triisocyanate, tris(isocyanatephenyl)thio-phosphate, lysine ester triisocyanate, 1,3,6-hexamethylene triisocyanate, 1,6,11-undecane triisocyanate, 1,8-diisocyanate-4-isocyanate methyloctane, and bicycloheptane triisocyanate) and tetraisocyanates (e.g., tetraisocyanate silane). These may be used alone or in combination of two or more thereof. It may also be possible to use a polymerized diisocyanate. As used herein, the term 'polymerized diisocyanate' refers to any of polymerized isocyanate derivatives produced by addition of three or more molecules of diisocyanate, or refers to a mixture of the isocyanate derivatives. For example, the isocyanate derivative may be of (1) trimethylolpropane adduct type, (2) biuret type, (3) isocyanurate type, or the like.

When the diisocyanate and the trifunctional isocyanate compound are used in combination, it is preferable to blend the former/the latter at a ratio of 19/1 to 1/1 (weight ratio).

A high molecular weight polyoi may be used as long as the object of the present invention is not impaired. As the high molecular weight polyol, a high molecular weight polyol having 3 or more hydroxyl groups may be used in order to introduce a crosslinking point into the liquid-crystal polyurethane elastomer to form a network. The number of hydroxyl groups is preferably 3. Examples of the high molecular weight polyol include polyether polyol, polyester polyol, polycarbonate polyol, polyester polycarbonate polyol, and the like. These may be used singly, or two or more of them may be used in combination.

In addition to the high molecular weight polyol, an active hydrogen group-containing low molecular weight compound may be used as long as the object of the present invention is not impaired. The active hydrogen group-containing low molecular weight compound is a compound having a molecular weight of less than 400, and examples thereof include low molecular weight polyols such as ethylene glycol, 1,2-propylene glycol, 1,3-propylene glycol, 1,2-butanediol, 1,3-butanediol, 1,4-butanediol, 2,3-butanediol, 1,6-hexanediol, neopentyl glycol, 1,4-cyclohexanedimethanol, 3-methyl-1,5-pentanediol, diethylene glycol, triethylene glycol, 1,4-bis(2-hydroxyethoxy)benzene, trimethylolpropane, glycerol, 1,2,6-hexanetriol, pentaerythritol, tetramethyiolcyclohexane, methyl glucoside, sorbitol, mannitol, dulcitol, sucrose, 2,2,6,6-tetrakis(hydroxymethyl) cyclohexanol, diethanolamine, N-methyldiethanolamine, and triethanolamine; low molecular weight polyaraines such as ethylenediamine, tolylenediamine, diphenylmethanediamine, and diethylenetriamine; alcohol amines such as monoethanolamine, 2-(2-aminoethylamino)ethanol, and monopropanolamine. These active hydrogen group-containing low molecular weight compounds may be used singly, or two or more of them may be used in combination.

The content of the liquid-crystal compound in a polyurethane raw material composition is preferably from 50 to 90% by weight, more preferably from 60 to 80% by weight. The polyurethane raw material composition is prepared by mixing raw material components under solvent-free conditions.

The liquid-crystal polyurethane elastomer may be produced by a prepolymer method or may be produced by a one-shot method. Incidentally, a catalyst promoting a known urethane reaction, such as tertiary amine type catalyst, may be used.

The liquid-crystal polyurethane elastomer is obtained by heating a polyurethane raw material composition and curing the composition by urethanication reaction. Then, during the urethanization reaction, the mesogenic groups of the liquid-crystal compound are oriented in a uniaxial direction while the liquid-crystal compound exhibits liquid crystallinity, and the composition is cured with the mesogenic group being in an oriented state. There is no particular limitation on the method of orienting the mesogenic group in the uniaxial direction, and examples of such a method include a method of performing the urethanization reaction on the oriented film, a method of orientation by applying an electric or magnetic field at the time of urethanization reaction, a method of stretching in the semi-cured state.

The transition temperature (Ti) from a liquid-crystal phase to an isotropic phase or from the isotropic phase to the liquid-crystal phase of the thermally responsive material of the present invention is preferably from 0 to 100° C., more preferably from 0 to 85° C.

EXAMPLES

Description will be given of the invention with examples, while the invention is not limited to description in the examples.

[Measurement and Evaluation Method]

(Calculation of Content of Liquid-Crystal Compound)

The content of the liquid-crystal compound in the polyurethane elastomer was calculated by the following expression.

Content (% by weight) of liquid-crystal compound={(Weight of liquid-crystal compound)/(Weight of all raw material components of polyurethane elastomer)}×100

(Measurement of (Liquid-Crystal Phase)-to-(Isotropic Phase) Transition Temperature (Ti) of Liquid-crystal Compound and Polyurethane Elastomer)

The Ti was measured under the condition of 20° C./min using a differential scanning calorimeter DSC (manufactured by Hitachi High-Tech science Corp., trade name: X-DSC 7000).

(Evaluation of Liquid Crystallinity)

The presence or absence of liquid crystallinity of the liquid-crystal compound and polyurethane elastomer were evaluated by using a polarization microscope (manufactured by Nikon Corporation, trade name: LV-100POL) and a differential scanning calorimeter DSC (manufactured by Hitachi High-Tech Science Corp., trade name: X-DSC 7000) under the condition of 20° C./min.

(Measurement of Storage Elastic Modulus (E') when Liquid Crystallinity is Exhibited)

The storage elastic modulus of the polyurethane elastomer when the liquid crystallinity is exhibited was measured under conditions of 2° C./min, strain 2%, and 10 Hz using a VES (trade name: Full Automatic Viscoelasticity Analyzer VR-7110, manufactured by Ueshima Seisakusho Co., Ltd.).

Example 1

Synthesis of Mesogenic Diol A, Liquid-Crystal Compound

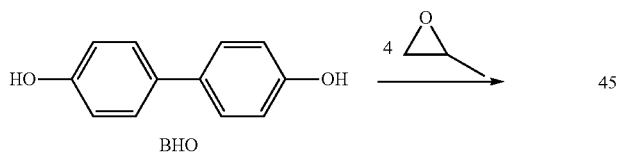

BHO

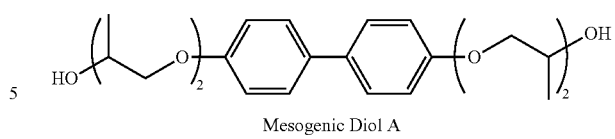

Mesogenic Diol A

To a reaction vessel were added 100 g of 4,4'-biphenol (BHO), 3.8 g of KOH and 600 ml of DMF, and then 4 equivalents of propylene oxide was added thereto relative to 1 mole of 4,4'-biphenol. The resulting mixture was allowed to react at 120° C. for 2 hours. Subsequently, 3.0 g of oxalic acid was added to the reaction solution to stop the addition reaction. After removal of the salt by suction filtration, the filtrate was evaporated under reduced pressure to remove the DMF, thereby obtaining a mesogenic diol A (which may contain a structural isomer).

(Synthesis of Polyurethane Elastomer)

A mixture was obtained from 2 g of mesogenic did A, 0.92 g of hexamethylene diisocyanate, and 0.10 g of HDI type isocyanurate (Sumidur N3300, manufactured by Sumika Bayer Urethane Co., Ltd.) by mixing them at 100° C. Thereafter, the mixture was poured into a mold preheated to 100° C. and was reacted to cure at 100° C. for 30 minutes to obtain a semi-cured polyurethane. After releasing the semi-cured polyurethane from the mold, the polyurethane was elongated twice in the uniaxial direction at 20° C. Thereafter, a polyurethane elastomer was obtained by allowing the polyurethane to stand at 20° C. until it was cured while maintaining the state of being twice elongated.

Example 2

A polyurethane elastomer was obtained in the same manner as in Example 1 except that the raw materials and compositions shown in Table 1 were employed.

Example 3

Synthesis of Mesogenic Diol B, Liquid-Crystal Compound

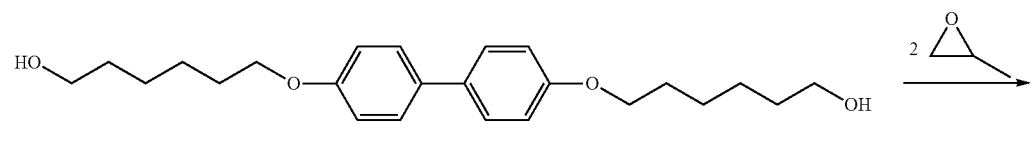

BH6

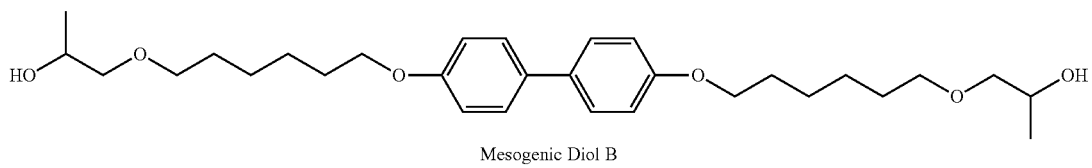

Mesogenic Diol B

To a reaction vessel were added 100 g of BH6, 3.8 g of KCH and 600 ml of DMF, and then 2 equivalents of propylene oxide was added thereto relative to 1 mole of BH6. The resulting mixture was allowed to react at 120° C. for 2 hours under pressure. Subsequently, 3.0 g of oxalic acid was added to the reaction solution to stop the addition reaction. After removal of the salt by suction filtration, the filtrate was evaporated under reduced pressure to remove the DMF, thereby obtaining a mesogenic diol B (which may contain a structural isomer).

(Synthesis of Polyurethane Elastomer)

A mixture was obtained from 2 g of mesogenic diol B, 0.79 g of hexamethyiene diisocyanate, and 0.09 g of HDI type isocyanurate (sumidur N3300, manufactured by sumika Bayer Urethane Co., Ltd.) by mixing them at 100° C. Thereafter, the mixture was poured into a mold preheated to 100° C. and was reacted to cure at 100° C. for 30 minutes to obtain a semi-cured polyurethane. After releasing the semi-cured polyurethane from the mold, the polyurethane was elongated twice in the uniaxial direction at 20° C. Thereafter, a polyurethane elastomer was obtained by allowing the polyurethane to stand at 20° C. until it was cured while maintaining the state of being twice elongated.

Examples 4 to 12

A polyurethane elastomer was obtained in the same manner as in Example 1 except that the raw materials and compositions shown in Table 1 were employed. In Table 1, TDI is toluene diisocyanate and MDI is diphenyl methane diisocyanate.

Example 13

Synthesis of Mesogenic Diol C, Liquid-Crystal Compound

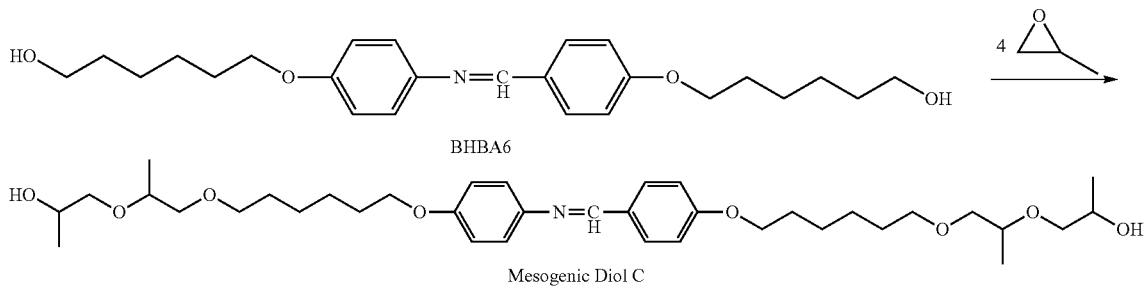

BHBA6

Mesogenic Diol C

To a reaction vessel were added 100 g of BHBA6, 3.8 g of KOH and 600 ml of DMF, and then 4 equivalents of propylene oxide was added thereto relative to 1 mole of BHBA6. The resulting mixture was allowed to react at 120° C. for 2 hours under pressure. Subsequently, 3.0 g of oxalic acid was added to the reaction solution to stop the addition reaction. After removal of the salt by suction filtration, the filtrate was evaporated under reduced pressure to remove the DMF, thereby obtaining a mesogenic diol C (which may contain a structural isomer).

(Synthesis of Polyurethane Elastomer)

A mixture was obtained from 2 g of mesogenic diol C, 0.59 g of hexamethyiene diisocyanate, and 0.07 g of HDI type isocyanurate (Sumidur N3300, manufactured by Sumika Bayer Urethane Co., Ltd.) by mixing them at 100° C. Thereafter, the mixture was poured into a mold preheated to 100° C. and was reacted to cure at 100° C. for 30 minutes to obtain a semi-cured polyurethane. After releasing the semi-cured polyurethane from the mold, the polyurethane was elongated twice in the uniaxial direction at 20° C. Thereafter, a polyurethane elastomer was obtained by allowing the polyurethane to stand at 20° C. until it was cured while maintaining the state of being twice elongated.

Example 14

Synthesis of Mesogenic Diol D, Liquid-Crystal Compound

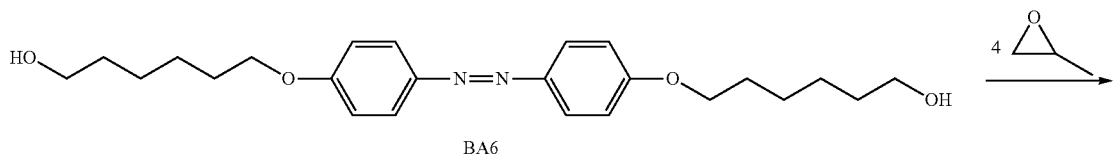

BA6

-continued

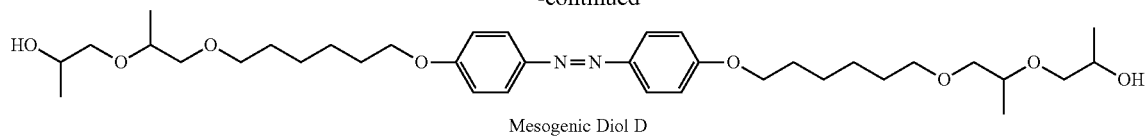
Mesogenic Diol D

To a reaction vessel were added 100 g of BA6, 3.8 g of KOH and 600 ml of DMF, and then 4 equivalents of propylene oxide was added thereto relative to 1 mole of BA6. The resulting mixture was allowed to react at 120° C. for 2 hours under pressure. Subsequently, 3.0 g of oxalic acid was added to the reaction solution to stop the addition reaction. After removal of the salt by suction filtration, the filtrate was evaporated under reduced pressure to remove the DMF, thereby obtaining a mesogenic diol D (which may contain a structural isomer).

(Synthesis of Polyurethane Elastomer)

A mixture was obtained from 2 g of mesogenic diol D, 0.59 g of hexamethyiene diisocyanate, and 0.07 g of HDI type isocyanurate (Sumidur N3300, manufactured by Sumika Bayer Urethane Co., Ltd.) by mixing them at 100° C. Thereafter, the mixture was poured into a mold preheated to 100° C. and was reacted to cure at 100° C. for 30 minutes to obtain a semi-cured polyurethane. After releasing the semi-cured polyurethane from the mold, the polyurethane was elongated twice in the uniaxial direction at 20° C. Thereafter, a polyurethane elastomer was obtained by allowing the polyurethane to stand at 20° C. until it was cured while maintaining the state of being twice elongated.

Comparative Examples 1 to 6

An attempt was made to prepare a polyurethane elastomer by using the raw materials shown in Table 1 in the same manner as in Example 1, but a polyurethane elastomer could not be prepared in the absence of a solvent since Ti of the mesogenic diol was high. BH3 to BH5 to BH11 in Table 1 are the following compounds.

BH3: a compound in which X is OH, $R_1$ is a single bond, $R_2$ is —O—, and $R_3$ is an alkylene group having 3 carbon atoms in the general formula (1).

BH4: a compound in which X is OH, $R_1$ is a single bond, $R_2$ is —O—, and $R_3$ is an alkylene group having 4 carbon atoms in the general formula (1).

BH5: a compound in which X is OH, $R_1$ is a single bond, $R_2$ is —O—, and $R_3$ is an alkylene group having 5 carbon atoms in the general formula (1).

BH11: a compound in which X is OH, $R_1$ is a single bond, $R_2$ is —O—, and $R_3$ is an alkylene group having 11 carbon atoms in the general formula (1).

TABLE 1

| | Mesoogenic diol | | | | | Composition of raw material | | | | | Polyurethane elastomer | |
| | | | | | | | | | | | Storage modulus during | Content of |
| | Mesogenic structure | Kind of oxide | Equivalent of addition oxide | Ti (° C.) | Liquid crystallinity | Mesogenic diol (g) | Diisocyanate (g) | N3300 (g) | Ti (° C.) | Liquid crystallinity | exhibiting liquid crystallinity (MPa) | mesogenic diol (%) |
|---|---|---|---|---|---|---|---|---|---|---|---|---|
| Example 1 | BH0 | Propylene oxide | 4 | 73 | Yes | 2 | HDI (0.92) | 0.1 | 35 | Yes | 1-100 | 66 |
| Example 2 | BH0 | Ethylene oxide | 2 | 145 | Yes | 2 | HDI (1.24) | 0.14 | 70 | Yes | 1-100 | 69 |
| Example 3 | BH6 | Propylene oxide | 2 | 102 | Yes | 2 | HDI (0.79) | 0.09 | 67 | Yes | 1-100 | 69 |
| Example 4 | BH6 | Propylene oxide | 4 | 81 | Yes | 2 | HDI (0.69) | 0.08 | 44 | Yes | 1-100 | 72 |
| Example 5 | BH6 | Propylene oxide | 4 | 81 | Yes | 2 | TDI (0.71) | 0.08 | 54 | Yes | 1-100 | 72 |
| Example 6 | BH6 | Propylene oxide | 4 | 81 | Yes | 2 | MDI (1) | 0.11 | 56 | Yes | 1-100 | 64 |
| Example 7 | BH6 | Propylene oxide | 6 | 63 | Yes | 2 | HDI (0.53) | 0.06 | 33 | Yes | 0.1-10 | 77 |
| Example 8 | BH6 | Propylene oxide | 6 | 63 | Yes | 2 | TDI (0.5) | 0.06 | 36 | Yes | 0.1-10 | 78 |
| Example 9 | BH6 | Propylene oxide | 8 | 43 | Yes | 2 | HDI (0.48) | 0.05 | 21 | Yes | 0.01-1 | 79 |
| Example 10 | BH6 | Propylene oxide | 8 | 43 | Yes | 2 | TDI (0.5) | 0.06 | 28 | Yes | 0.01-1 | 76 |
| Example 11 | BH6 | Butylene oxide | 5 | 76 | Yes | 2 | HDI (0.52) | 0.06 | 19 | Yes | 1-100 | 78 |
| Example 12 | BH6 | Styrene oxide | 2 | 125 | Yes | 2 | HDI (0.62) | 0.07 | 75 | Yes | 1-100 | 74 |
| Example 13 | BHBA6 | Propylene oxide | 4 | 72 | Yes | 2 | HDI (0.59) | 0.07 | 38 | Yes | 1-100 | 75 |
| Example 14 | BA6 | Propylene oxide | 4 | 76 | Yes | 2 | HDI (0.59) | 0.07 | 42 | Yes | 1-100 | 75 |

TABLE 1-continued

| | Mesogenic diol | | | | | Composition of raw material | | | Polyurethane elastomer | | |
|---|---|---|---|---|---|---|---|---|---|---|---|
| | Mesogenic structure | Kind of oxide | Equivalent of addition oxide | Ti (° C.) | Liquid crystal-linity | Meso-genic diol (g) | Diiso-cyanate (g) | N3300 (g) | Ti (° C.) | Liquid crystal-linity | Storage modulus during exhibiting liquid crystallinity (MPa) | Content of meso-genic diol (%) |
| Comparative Example 1 | BH0 | — | — | — | None | — | — | — | — | — | — | — |
| Comparative Example 2 | BH3 | — | — | 208 | Yes | — | — | — | — | — | — | — |
| Comparative Example 3 | BH4 | — | — | 189 | Yes | — | — | — | — | — | — | — |
| Comparative Example 4 | BH5 | — | — | 170 | Yes | — | — | — | — | — | — | — |
| Comparative Example 5 | BH6 | — | — | 172 | Yes | — | — | — | — | — | — | — |
| Comparative Example 6 | BH11 | — | — | 160 | Yes | — | — | — | — | — | — | — |

INDUSTRIAL APPLICABILITY

Since the thermally responsive material of the present invention exhibits a characteristic response behavior of shrinking in the orientation direction when reducing the orientation degree of the liquid-crystal by applying heat and elongating in the orientation direction when removing the heat to increase the orientation degree of the liquid-crystal, the thermally responsive material can be applied to various fields such as actuators and the like.

The invention claimed is:

1. A liquid-crystal compound obtained by adding an alkylene oxide and/or styrene oxide to a mesogenic group-containing compound represented by a general formula (1) below:

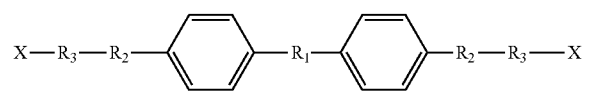

(1)

wherein X is an active hydrogen group; $R_1$ is a single bond, —N=N—, —CO—, —CO—O—, or —CH=N—; $R_2$ is a single bond or —O—; and $R_3$ is an alkylene group having 1 to 20 carbon atoms.

2. The liquid-crystal compound according to claim 1, wherein the alkylene oxide is at least one kind selected from the group consisting of ethylene oxide, propylene oxide, and butylene oxide.

3. The liquid-crystal compound according to claim 2, wherein 2 to 10 moles of the alkylene oxide and/or styrene oxide are added to 1 mole of the compound represented by the general formula (1).

4. A thermally responsive material obtained by reacting the liquid-crystal compound according to claim 1 with a compound that reacts with an active hydrogen group of the liquid-crystal compound.

5. The thermally responsive material according to claim 4, comprising 50 to 90% by weight of the liquid-crystal compound as a raw material.

6. The thermally responsive material according to claim 4, wherein a transition temperature from a liquid-crystal phase to an isotropic phase or from an isotropic phase to a liquid-crystal phase is from 0 to 100° C.

7. A thermally responsive material obtained by reacting the liquid-crystal compound according to claim 1 with a compound that reacts with an active hydrogen group of the liquid-crystal compound.

8. The thermally responsive material according to claim 7, comprising 50 to 90% by weight of the liquid-crystal compound as a raw material.

9. The thermally responsive material according to claim 7, wherein a transition temperature from a liquid-crystal phase to an isotropic phase or from an isotropic phase to a liquid-crystal phase is from 0 to 100° C.

* * * * *